United States Patent
Hesse

(10) Patent No.: US 11,980,732 B2
(45) Date of Patent: May 14, 2024

(54) URINARY PLUG DEVICE

(71) Applicant: David Hesse, Branford, CT (US)

(72) Inventor: David Hesse, Branford, CT (US)

(*) Notice: Subject to any disclaimer, the term of this patent is extended or adjusted under 35 U.S.C. 154(b) by 161 days.

(21) Appl. No.: 17/543,236

(22) Filed: Dec. 6, 2021

(65) Prior Publication Data

US 2022/0087805 A1  Mar. 24, 2022

Related U.S. Application Data

(63) Continuation of application No. 16/836,185, filed on Mar. 31, 2020, now Pat. No. 11,246,693.

(51) Int. Cl.
  *A61M 31/00* (2006.01)
  *A61F 2/00* (2006.01)
  (Continued)

(52) U.S. Cl.
  CPC ......... *A61M 31/002* (2013.01); *A61F 2/0009* (2013.01); *A61F 13/2071* (2013.01); *A61F 13/2074* (2013.01); *A61F 13/34* (2013.01); *A61F 2002/048* (2013.01); *A61F 2013/2014* (2013.01); *A61F 2210/0004* (2013.01);
  (Continued)

(58) Field of Classification Search
  CPC .. A61F 5/44; A61F 5/48; A61F 2/0009; A61F 2210/0004; A61F 2310/0097; A61F 2230/0069; A61F 2210/0076; A61F 13/2071; A61F 13/2074; A61F 13/34; A61F 2002/048; A61F 2013/2014; A61M 31/002; A61M 25/0017; A61M 2210/1082
  See application file for complete search history.

(56) References Cited

U.S. PATENT DOCUMENTS 4,413,995 A * 11/1983 Korpman ............... A61F 13/534
  428/913
5,090,424 A    2/1992 Simon et al.
  (Continued)

FOREIGN PATENT DOCUMENTS

EP    0193406 B1    2/1991
WO    9426215 A1    11/1994
  (Continued)

OTHER PUBLICATIONS

Onofrei, M., and A. Filimon. "Cellulose-based hydrogels: designing concepts, properties, and perspectives for biomedical and environmental applications." Polymer science: research advances, practical applications and educational aspects (2016): pp. 108-120.
(Continued)

*Primary Examiner* — Yashita Sharma
(74) *Attorney, Agent, or Firm* — Murtha Cullina LLP

(57) ABSTRACT

A disposable device for absorbing urine and/or bodily fluids in the urethra having a cylindrical body having a top and bottom end. The body is made of absorbent material that expands upon contact with urine and bodily fluids and includes a string connected to the bottom end of the body for removing the device from the urethra. The device can include a vasodilator in or on a surface of the body and can be used to treat urinary incontinence and/or erectile dysfunction by inserting into the urethra and removing the device after it has been impregnated with fluid. The device can be included in a kit with a plunger for insertion.

16 Claims, 11 Drawing Sheets

(51) Int. Cl.
*A61F 13/20* (2006.01)
*A61F 13/34* (2006.01)
*A61F 2/04* (2013.01)
*A61M 25/00* (2006.01)

(52) U.S. Cl.
CPC ............... *A61F 2210/0076* (2013.01); *A61F 2230/0069* (2013.01); *A61F 2310/0097* (2013.01); *A61M 25/0017* (2013.01); *A61M 2210/1082* (2013.01)

(56) References Cited

U.S. PATENT DOCUMENTS

| | | |
|---|---|---|
| 5,800,338 A | 9/1998 | Kollerup et al. |
| 5,887,593 A | 3/1999 | Levius |
| 6,656,146 B1 | 12/2003 | Clayman et al. |
| 6,676,593 B2 | 1/2004 | Migachyov et al. |
| 6,679,831 B1 | 1/2004 | Zunker et al. |
| 8,247,638 B2 | 8/2012 | Kim et al. |
| 9,610,201 B2 | 4/2017 | Schmidt-Foerst et al. |
| 9,707,065 B2 | 7/2017 | Kunz |
| 10,195,091 B2 | 2/2019 | Rosati et al. |
| 2001/0014797 A1 | 8/2001 | Suzuki et al. |
| 2002/0156343 A1 | 10/2002 | Zunker |
| 2002/0156442 A1 | 10/2002 | Jackson et al. |
| 2003/0191442 A1 | 10/2003 | Bewick-Sonntag et al. |
| 2004/0078013 A1 | 4/2004 | Zunker et al. |
| 2005/0090794 A1 | 4/2005 | Dyer et al. |
| 2005/0113781 A1 | 5/2005 | Forgeot et al. |
| 2006/0216334 A1* | 9/2006 | Gehling .............. A61F 13/2051 424/443 |
| 2007/0016163 A1 | 1/2007 | Santini, Jr. et al. |
| 2008/0077174 A1 | 3/2008 | Mische |
| 2009/0318750 A1 | 12/2009 | Ziv et al. |
| 2010/0100170 A1 | 4/2010 | Tan et al. |
| 2010/0185154 A1 | 7/2010 | Tewari |
| 2011/0028778 A1 | 2/2011 | Kunz |
| 2012/0259160 A1 | 10/2012 | Karapasha |
| 2012/0290100 A1 | 11/2012 | Li |
| 2013/0211185 A1 | 8/2013 | Hull, Jr. et al. |
| 2016/0361191 A1 | 12/2016 | Moon |
| 2018/0042742 A1 | 2/2018 | Venkatraman et al. |
| 2019/0240063 A1 | 8/2019 | Doreswamy et al. |

FOREIGN PATENT DOCUMENTS

| | | |
|---|---|---|
| WO | 2016005824 A1 | 1/2016 |
| WO | 2017134094 A1 | 8/2017 |

OTHER PUBLICATIONS

International Search Report and Written Opinion for PCT Application No. PCT/US2020/051545 dated Dec. 3, 2020.
ArmMed Media, Urinary Incontinence, "Managing Urinary Incontinence", Retrieved on Oct. 29, 2019: http://www.health.am/gyneco/more/managing-urinary-incontinence/ (6 pages total).
Nancy M. Shinopulos et. al, "Patient Selection and Education for Use of the CapSure (Re/Stor) Continence Shield", Urologic Nursing, vol. 19, No. 2, pp. 135-140, Jun. 1999.
Examination Report from Canadian Patent Office for Application No. 3,151,741 dated Jul. 7, 2023.
Extended European Search Report for Application No. EP 20866407.8 dated Oct. 6, 2023.

* cited by examiner

URINARY PLUG DEVICE

FIELD OF THE INVENTION

The invention relates to a device that blocks the passageway that drains urine in men or women and/or the ureters, and methods of addressing urinary incontinence and erectile dysfunction, and tumors, stones, and cancers in the urinary organs, by inserting the inventive devices into the urethra or ureters.

BACKGROUND OF THE INVENTION

The Global Incontinence Forum suggests that if urinary incontinence were a country, it would be the third largest in the world, after China and India. Worldwide, urinary incontinence is estimated to affect 12.4% of women and 5% of men, with 8.7% of people greater than 20 years of age, or 423 million people affected (Irwin, et.al, BJU Int 2011 October; 108 (7) 1132-8). Urinary incontinence is thought to affect 15 million women in the US. The number of men with significant urinary incontinence in the US is less well known, as up to 50% of people don't report urinary incontinence to their health care providers. There are many different types of urinary incontinence: stress, urge, combination of stress/urge, and noncompliant "stovepipe" urethras (which results in total gravity incontinence). The social stigma and personal hygiene issues associated with urinary incontinence are not dissimilar to a woman unprotected from menstrual flow. Shame, isolation, depression, and adverse health related issues arise when urinary incontinence is unsuccessfully treated or ignored.

There are several alternative treatments available to manage urinary incontinence: 1) pelvic exercise and biofeedback techniques are low cost but meet with only limited success, and usually only in people with very mild stress and/or urge incontinence; 2) prescription medication can be used to manage urge incontinence, but is associated with side effects such as constipation, dry mouth, and cognitive changes, and can be expensive; 3) peri-urethral bulking agents using collagen or hyaluronic acid are used to manage stress incontinence and non-compliant urethras in men and women, but require general anesthesia to surgically percutaneously inject tissue with compound and usually have limited success; 4) urethral slings and bladder neck slings using either autologous, cadaver or synthetic material are often successful at treating stress and noncompliant urethra in men and women, but requires surgery and are expensive: 5) artificial urinary sphincters are surgically placed for noncompliant urethras when the patient is totally incontinent. This procedure requires specialized surgery and is expensive; 6) penile clamps (Cunningham clamp) are available to men with significant urinary incontinence, usually related to a noncompliant urethra, assuming their penis has sufficient length to use the clamp. The device is reusable, cheap, but uncomfortable. There is poor patient compliance with this device; 7) vaginal inserts, for example Poise Impressa, are non-prescription devices that externally compress the urethra by applying pressure on the roof of the vagina. Other proposed externally occlusive urethra devices require anchors to either the bladder or external tissue; 8) men can use external condom catheters to collect urine to be drained into collection receptacles. The condom catheter is a plastic or rubber device that covers the penis down to the base of penile shaft, and requires adhesive to allow device to stay in place. Body habitus must allow for sufficient penile girth for device to be properly placed. The device is inexpensive but cumbersome to place, and often becomes dislodged with movement; 9) internal catheters can be placed through the urethra in men and women, anchored in place to the bladder neck by inflating a balloon at the end of the catheter through a side-port of catheter. Catheters can then be attached to a receptacle to collect urine. Indwelling catheters are associated with discomfort and are cumbersome. They often require placement by a health care professional. Chronic indwelling catheters are associated with increased urinary tract infection and urethral erosion; 10) various urethral plugs have been described made of silicone or other material that anchor the plug via a balloon inflated within the bladder neck. Femsoft is a commercially available product that uses this technology. It has met with limited success. It requires a prescription. Balloon inflation at the bladder neck often causes bladder trigone irritation and pain; 11) diapers. Diapers are cheap and do not require a prescription to be obtained. Diapers, however, are bulky, malodorous, associated with pelvic skin irritation, and difficult to dispose.

U.S. Patent Application Publication No. 2001/0014797 discloses incontinence pads containing super absorbent polymers (SAPs) to absorb large or small amounts of urine. Pads are not discreet and are used outside the urethra.

International Patent Application Publication WO 1994026215 by Uromed Corp. is directed to balloons for blocking the urethra. It describes an expandable deformable member (sponge) made of hydrophilic material which expands when moisture contacts it. The device, as illustrated in embodiments 1 through 3, would be difficult to manufacture and they rely on a cumbersome string apparatus. Patients would be required to manipulate different strings to activate/deactivate device, much like a two string system used to raise and lower Venetian blinds. Embodiments 4 and 5 rely on coupling of proximal thermo-sensitive plug or sponge to a solid polyurethane cylindrical shaft with a distal meatal plate. Advancing a solid shaft up urethra is potentially dangerous, as minimal torqueing of the solid shaft could injure the urethra. Moreover, a meatal plate at urethral meatus would be uncomfortable and risk abrading delicate meatal tissue. Also, because the device is intended to be reusable, issues of the ability to satisfactorily disinfect a reusable plug are to be questioned, especially if a sponge is used as the plug.

EP 0193406 to Medtronic, Inc. is directed to a urethral plug that comprises a hydrophilic, body fluid swelling hydrogel. However, this is aimed at a plug rather than a disposable absorber. Moreover, it would be cumbersome for patient to place the device as patients must activate a plunger and at same time make sure radial flanges or flaps are disengaged from device. As noted with the previous device, radial flanges or flaps, intended to serve as an umbrella at meatus and prevent migration of a device into the bladder, would be uncomfortable and risk abrading delicate meatal tissue. Furthermore, all hydrophilic hydrogels proposed for this device are non-biodegradable and therefore not optimal for disposable product.

There are reports of vaginal tampons being accidentally inserted into the urethra. These tampons are much too large for the opening and cause pain. Moreover, vaginal tampons are not designed to absorb urine or the amounts of liquid discharged by many with incontinence issues.

U.S. Pat. No. 5,800,338 generally discloses the concept of a tampon or closure device that could be inserted into the urethra. The body of the device is provided with a withdrawal handle means protruding from the body and connected with an anchor part encapsulated in the body and having a relatively large bearing face against the surrounding molded material of the body. The handle and anchor part are made from a material with a knitted structure, to provide a three-dimensional bond to the molded material of the body. The anchor part is designed as a soft flexible element oriented in said longitudinal direction. However, no details are provided of how a urethral device would differ from one suited for vaginal or anal insertion and a physical embodiment of a urethral device is heretofore unknown by the inventor.

There is a need for incontinence materials that are discreet and can be inserted in the urethra, rather than the vagina.

There is a need for incontinence devices that can comfortably be inserted into the urethra and that do not abrade delicate meatal tissue.

There is a need for urethral plugs capable of absorbing the amounts of urine that are discharged in incontinent individuals, and blocking further urine from involuntarily draining from the bladder.

There is a need for disposable incontinence devices that eliminate sanitation concerns or reusable devices and that are environmentally friendly when disposed.

Erectile Dysfunction (ED) is another common condition treated by urologists affecting about 30 million men in the United States. The Massachusetts Male Aging Study suggests that 617,715 new cases of erectile dysfunction present in the US annually. There is an increased worry about this condition due to the aging population. Sexuality might wane for many older people but it doesn't completely go away. Fulfilling this need is important for many people who have life-long spouses.

Currently, there are five treatments for erectile dysfunction (ED): 1) phosphodiesterase type 5 (PDE5) inhibitors (Viagra, Levitra, Cialis, Stendra) that when taken orally often improve erectile function. These agents are expensive, and have side effects such as headache, facial flushing, indigestion, and hypotension when taken with nitroglycerin agents. 2) vacuum cylinder devices placed over penis that draw blood into penile shaft, followed by trapping of tumescent penis with rubber band device placed at base of penis. These devices are cumbersome to use and cause discomfort to male after 30 minutes. 3) penile injection therapy, where vasoactive medication is injected directly into penile shaft. This treatment is very effective, although risk of prolonged erection requiring emergency intervention occurs 10% of time. Also, many males are reluctant to inject their penis. 4) MUSE (vasoactive pellet injected into penile urethra with applicator. This treatment is only effective in 30% of men. Limited success with MUSE may be due to inadequate concentration of medication being absorbed into erectile tissue of penis. 5) Surgically placed penile prostheses. Surgery is expensive; many insurances will not cover this surgery. Risk of infection and mechanical breakdown of prostheses can occur.

Bladder cancer is one of the most common cancers, affecting approximately 68,000 adults in the United States each year. Bladder cancer occurs in men more frequently than it does in women and usually affects older adults, though it can happen at any age.

In contrast, cancers of the upper urinary tract are relatively rare but are difficult to treat.

There is need for devices and improved methods of treating upper urinary tract urothelial cancers, short of proceeding with surgical removal of kidney and ureter.

SUMMARY OF THE INVENTION

The foregoing is achieved by a device for insertion into the urethra of a mammal comprising: a substantially cylindrical body about 4-8 mm or 8-30 French scale ("Fr") in diameter by about 3-5 cm in length and having a proximal insertion end and a distal withdrawal end, said body comprised of absorbent material that expands upon contact with urine or bodily fluid; and a string connected to the distal end of the body for removing the device from the urethra.

In certain preferred embodiments, the diameter of the device is about 5 mm. In some alternative embodiments, the diameter is 14-22 Fr.

In some embodiments, the length of the body is about 3 cm; in other embodiments the length of the body is about 5 cm.

In preferred embodiments, the substantially cylindrical body is composed of outer layer of desiccated cotton, followed by an intermediate layer of desiccated chitosan or cellulose/bio-sponge material, followed by an innermost layer of absorbent material, preferably super absorbent polymer (SAP) or nanofiber materials, both with hydrogel physicochemical properties.

The device is encased in a mesh covering with a cotton string attached to one end. The mesh can be comprised or contained of polyethylene or other suitable materials known in the art. Other suitable string materials are also envisioned besides cotton and as disclosed in the vaginal and anal tampon arts.

At the tip of the proximal end is an optional small receptacle filled with hydrophilic anesthetic jelly, that is popped to coat the device just before use. This receptacle could also be filled with any other lubricating device suitable for the urethra.

Optionally, the proximal tip could alternatively or further contain an active agent, such as an antibiotic or vasodilator, such as alprostadil. Alternatively, the device could be impregnated with an antibiotic or vasodilator (such as alprostadil). Any agent suitable for transdermal administration is envisioned. To the extent the active agents have a tendency to react with the materials of the urethral device, the agents could be coated or encapsulated in materials that are compatible with the device materials. Suitable buffering materials and complexing agents are envisioned.

The device is preferably tailored to urethral dimensions of patient sex. A device for a female human urethra is approximate approximately 5 mm in diameter by 3 cm in length. A device for male urethra is 5 mm in diameter by 5 cm in length. Those in the veterinary arts will appreciate alternative dimensions for other mammals.

A similar device, measuring about 1-2 mm in diameter and about 1-2 mm in length, is more suitable for insertion into a ureter.

The proximal insertion tip is preferably tapered. The device for a urethra is manually placed approximately 3 to 5 cm into an anterior urethra, based on patient sex, just far enough into the urethra to allow the string alone to exit urethral meatus.

Alternatively, the device can be housed in an applicator, with plunger that expels device into urethra. If an applicator is used, a small receptacle filled with hydrophilic anesthetic jelly can be attached inside a proximal tip of the applicator to coat the cylindrical device as it is expelled into urethra.

Once placed in the anterior urethra, upon contact with urine, the device will expand to 100× to 700× its initial size. Absorbent properties of hydrogel polymers within the device will allow it to expand to internal volume of the anterior urethra. Further, the increased viscosity of hydrogel polymers within device will obstruct flow of urine from passing thru or around urethral insert. The device is removed by simply pulling a string extending from the distal end of the body. The device can be exchanged every 6 hours, or as needed, depending on sensation of bladder fullness.

Advantages of devices and methods disclosed herein are 1) easy to use requiring no special medical teaching, and can be easily placed by a person suffering incontinence; 2) minimal discomfort, as device is being placed in the anterior urethra. Pain with urethral manipulation occurs when objects are placed across (more proximal) urethral sphincter, or within bladder neck and floor or bladder trigone. This commonly occurs with other incontinence devices. No anchors or balloons are required to hold the device in place; 3) the device is not bulky or malodorous; 4) sexual activity can occur with the device in place; 5) the device is cheap to manufacture and not expensive to buy; 6) the device is completely biodegradable if nanofibers are used in the cylinder. If SAPs are used, these materials are recyclable.

Thus, the disclosed devices block the passageway that drains urine in men or women. The inventive devices are easy to insert and remove, do not require a prescription, are cheap to manufacture, not bulky, provide comfort and psychological wellbeing, and are biodegradable/recyclable.

If a male urethral plug is to be used for management of ED, different amounts of impregnated bioactive agents will need to be trialed, to find maximal clinical benefit coupled with minimal risk to patient.

If a urinary plug is used in the ureter, known chemotherapeutic or immunotherapeutic agents to treat urothelial cancer in the upper urinary tract will be feasible. Topical anti-cancer agents instilled in the bladder for bladder cancer decrease risk of patients requiring eventual radical cystectomy (bladder removal) by 25-75%. Similarly, by injecting anti-tumor agents into the ureter, followed by placing temporary ureteral plug to prevent drainage of medication and prolong intra-ureteral dwell time, surgical removal of kidney and ureter (nephroureterectomy) should decrease by 25-75%.

DETAILED DESCRIPTION OF THE INVENTION

The embodiments of the present invention will be described with reference to the accompanying drawings and below description.

Figure 1:
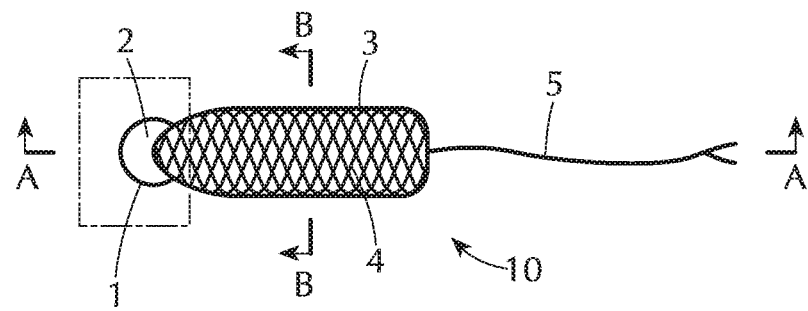
FIG. 1 is a side view of an absorbent device of the present invention.
Figure 5:
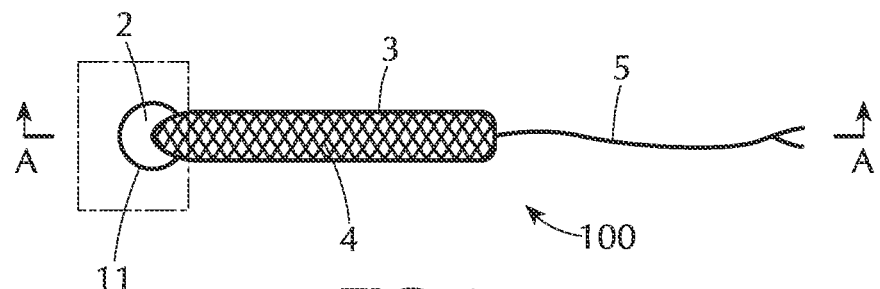
FIG. 5 is a side view of an absorbent device of the present invention.

Referring to FIGS. 1 and 5, a urine absorbing device 10, 100 suitable for a female and male, respectively, is depicted. The device 10, 100 contains a biodegradable receptacle 1, 11, lubricating material 2, mesh covering 3, cylindrical body 4 and a withdrawal cord 5.

The body 4 has an insertion end, a withdrawal end, a longitudinal axis, and an outer surface. As depicted in FIG. 1, the body 4 may contain a mesh covering 3 on or around the outer surface. Although shown as generally straight and cylindrical, the shape of the body may be straight or non-linear that curves along the longitudinal axis. A spiraled indentation into cylinder, e.g., may increase intra-urethral wall surface tension by increasing device surface area.

Figure 7A:
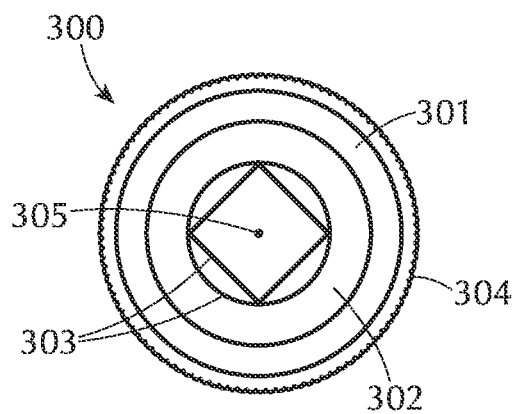
FIGS. 7A-7D are a cross sectional views of various embodiments of an absorbent device for insertion into the urethra along the radial axis.
Figure 7B:
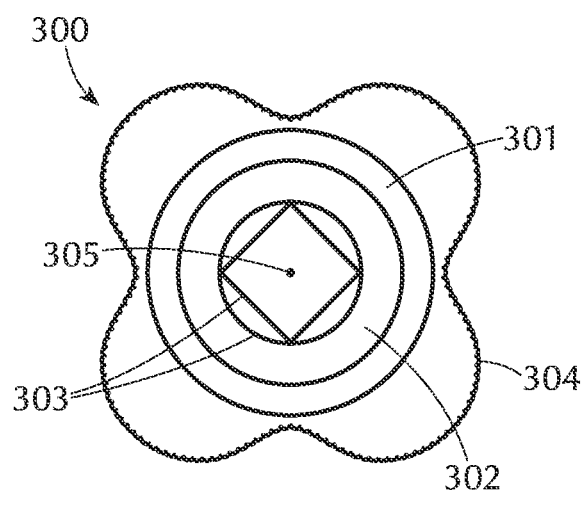
Figure 7C:
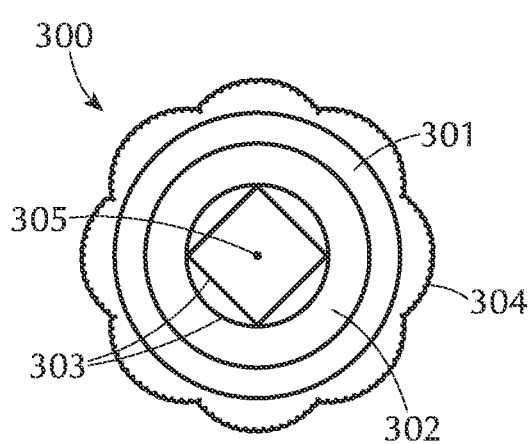
Figure 7D:
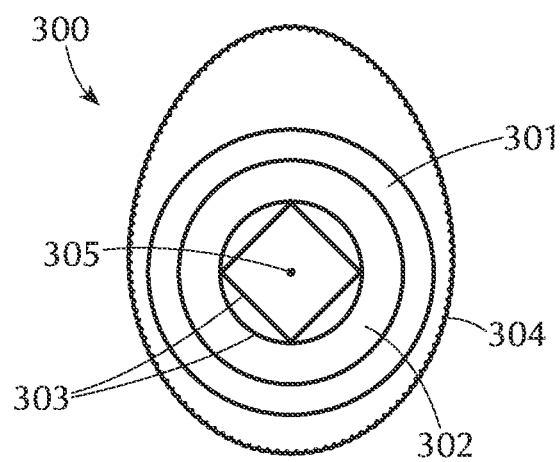

Other shapes are possible, such as those depicted in FIGS. 7B-7C. The bodies 304 may include shapes having a cross-section that can be described as rectangular, triangular, trapezoidal, semi-circular, hourglass-shaped, S-shaped, or other suitable shapes. The outer surface of the can be altered to have a non-uniform surface topography.

The "outer surface" refers to the visible surface of the body, which may be compressed and/or molded before use and/or expansion. At least a portion of the outer surface may be smooth, or alternatively may have ribs, spiral ribs, mesh patterns, etc., or other topographic features.

The body 4, 304 is comprised of absorbent material that expands upon contact with urine. A wide variety of liquid-absorbing materials used in absorbent articles are suitable, such as rayon, cotton, or comminuted wood pulp which is generally referred to as airfelt. Examples of other suitable absorbent materials include creeped cellulose wadding; meltblown polymers including conform; chemically stiffened, modified or cross-linked cellulosic fibers; synthetic fibers such as crimped polyester fibers; peat moss; tissue including tissue wraps and tissue laminates; or any equivalent material or combinations of materials, or mixtures of these. Preferred absorbent materials comprise cotton, rayon (including tri-global and conventional rayon fibers, and needle punched rayon), folded tissues, woven materials, nonwoven webs, synthetic and/or natural fibers.

The body 4, 304 may preferably be constructed of rayon or cotton or some combination of these. Suitable cotton material includes, long fiber cotton, short fiber cotton, cotton linters, T-fiber cotton, card strips, and comber cotton. Preferably, the cotton layers should be a scoured bleached cotton absorbent with a glycerin finish, a lemolin finish, or other suitable finish.

Figure 4:
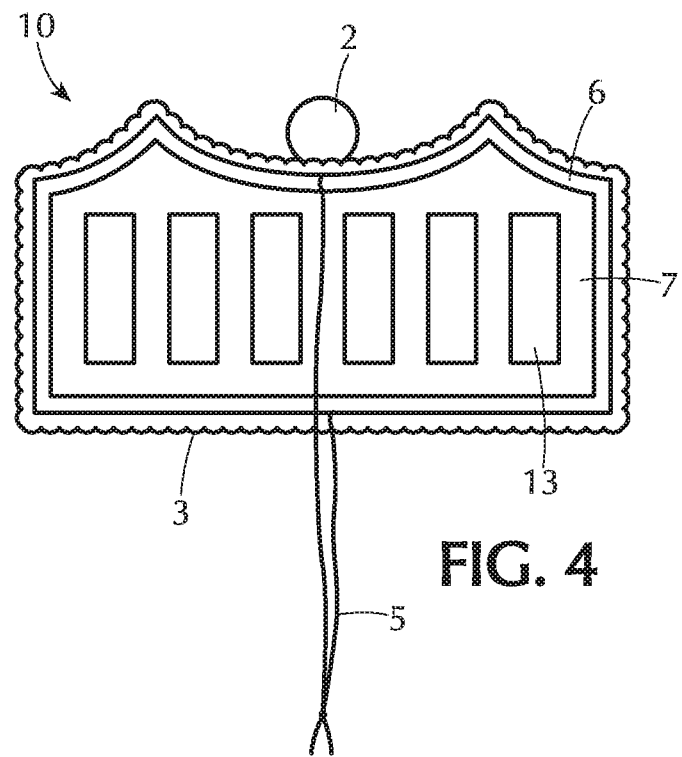
FIG. 4 is a cross-sectional view of the device of FIG. 1 along the axis A-A.
Figure 6:
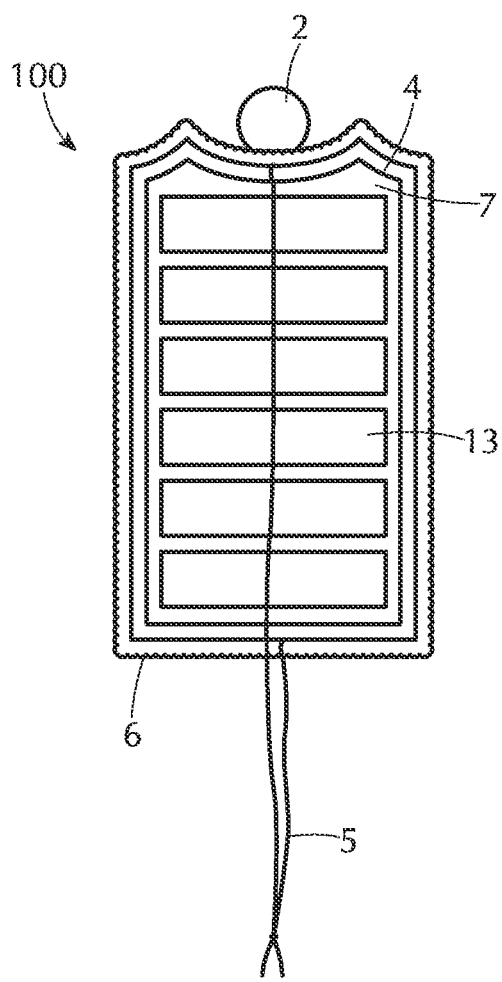
FIG. 6 is a cross-sectional view of a device of FIG. 5 along the axis A-A.

As shown in FIGS. 4 and 6, the body preferably contains a central absorbent core having a first end, a second end disposed opposite said first end, and a side surface extending between said first end and said second end, wherein said first end corresponds to an insertion end of said device, said side surface being oriented in a direction generally parallel to a longitudinally-extending central axis, said central absorbent core being constructed from an absorbent material compressed to a self-sustaining form; and a withdrawal cord joined to said device and extending therefrom.

As used herein, the term "longitudinal axis" refers to an axis A-A that passes through the center of the device, as shown in FIGS. 1 and 5. A portion of the device may be asymmetric about the longitudinal axis, such as when the withdrawal end region is twisted open from the initial shape of the rest of the device in a funnel shape (such as a "fin shape"). Further, the longitudinal axis may be linear or non-linear.

As used herein, the term "radial axis" of a device refers to an axis that runs perpendicular to the longitudinal axis of the device, shown as B-B in FIG. 1.

The length of the device can be measured along the longitudinal axis from the insertion end to the withdrawal end.

The withdrawal cord 5 may be attached to any suitable location on the device. The withdrawal cord, in one embodiment shown in FIG. 4, may be attached to the outer surface of the insertion end of the body. Alternatively, the attachment may be at the first end of the central absorbent core in one embodiment, or may be at the second end of the central absorbent core in other embodiments. In additional embodiments, multiple cords may be attached to the body and/or core allowing for both withdrawal and post-insertion manipulation of the absorbent device.

The withdrawal cord 5 may be made from any suitable material known in the prior art and may include cotton and rayon. In addition, the withdrawal cord 5 can take other forms such as ribbons, loops, tabs, and the like. The withdrawal cord may be integral with the body. The withdrawal cord 5 or a region of the withdrawal cord 5 may be treated to be non-absorbable, absorbent, or hydrophilic. The withdrawal cord 5 may be attached in any suitable manner known in the art, including suturing, adhesive attachment, bonding, thermal bonding, or combinations thereof.

The withdrawal cord 5 may be attached along the entire length and/or one major surface of the body and hang free from one end, such as the withdrawal end.

The term "attached", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; one element is essentially part of the other element.

In certain embodiments, the withdrawal cord 5 may be attached to the body using any suitable adhesive. Such adhesive may extend continuously along the length of attachment or it may be applied in a "dotted" fashion at discrete intervals. Alternatively, the cord 5 may be attached by stitching. Such stitching may use cotton or rayon thread. Other attachment mechanisms include thermally bonding, fusion bonding, or any other suitable means known in the art for joining such materials.

As shown in FIGS. 1 and 4-6, the device may contain a lubricating material 2 at the insertion end.

Any lubricant suitable for urological procedures is contemplated. In typical urological procedures, before inserting a device into the urethral orifice during examination or surgery, lidocaine jelly hydrochloride or lubricant is applied to the urethral orifice. The lubricating material 2 may be a hydrophilic anesthetic jelly (e.g. lidocaine jelly 1% pr 2%). A preferred lubricant is KY™ jelly. Alternatively, a water soluble lubricant such as SURGILUBE® surgical lubricant sterile bacteriostatic is contemplated. The lubricating material may additionally contain active agents, such as antibiotics, vasodilators, or cancer agents, as further discussed below.

Typically, about 1 to 2 mL of lubricant material will be sufficient. Those of skill in the art can adjust based on the patient and procedure.

The lubricant may be contained in a biodegradable receptacle 1, 11 attached to the insertion end of the body, preferably the tip of the insertion end, as shown in FIGS. 1 and 5. The receptacle 1, 11 is ideally made from a biodegradable or compostable plastic such as PLA (polylactic acid, or its polymers, made from fermented plant starch such as corn or sugarcane) filled with 1 to 2 cc's of viscous lidocaine 2%, or alternatively, a water soluble lubricant such as SURGILUBE®. It is also contemplated that other bio-based plastics such as PGA, PHAs, PBS, PCL, PVA PBAT, starch blends, cellulose esters and their derivatives, and lignin-based polymers may be used as alternatives or in conjunction with PLA.

In certain embodiments, a small force suffices to introduce lubricant 2 onto, and about the device, coating device. Finger pressure is adequate to express lubricant 2 from the biodegradable receptacle 1, 11.

The mesh covering 3 may be hydrophilic coated biodegradable mesh covering measuring approximately 6 mm by 2.5 cm. In some embodiments, the mesh is comprised of polyethylene. Other materials, such as polyurethane, may be utilized for mesh 3.

Figure 2:
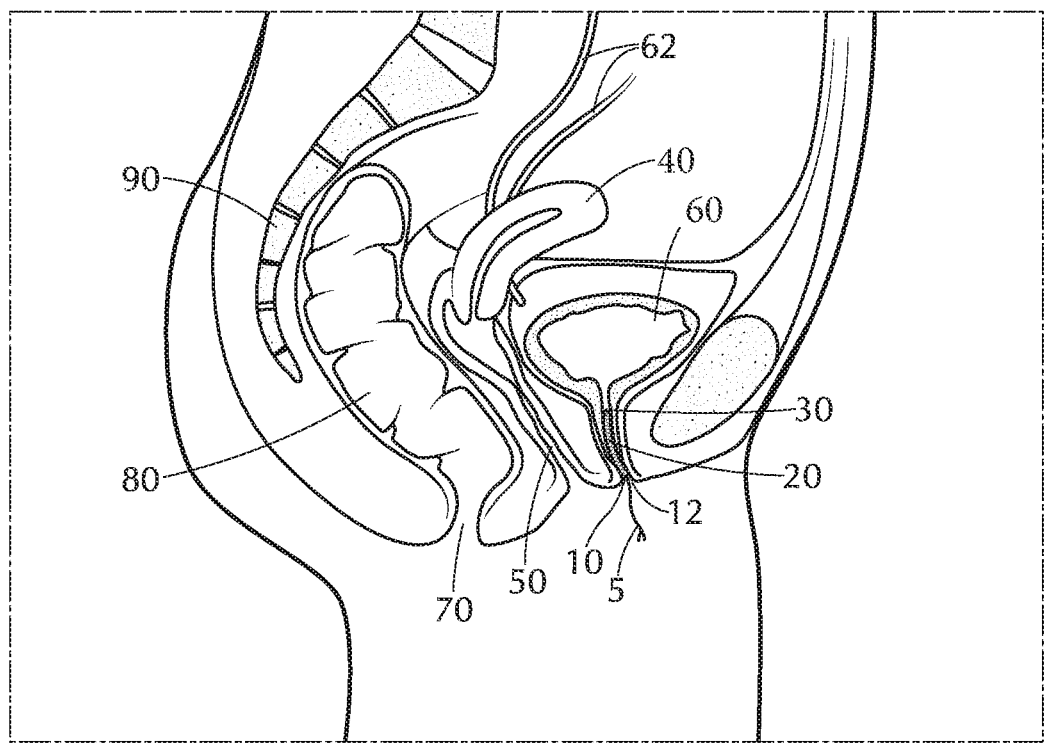
FIG. 2 is a cross section of a female pelvis, showing an absorbent device inserted into urethra.

With reference to FIG. 2, the female anatomy contains a urethral meatus 12, an anterior urethra 20, and a proximal urethra 30. Above the proximal urethra 30 is the bladder 60 and ureters 62. The uterus 40 and vagina 50 lie behind the bladder and urethra, respectively. On the posterior side is the anus 70 and the rectum 80. The device 10 is optimally positioned in the urethral opening and rests in the urethral meatus 12 and anterior urethra 20.

Figure 3:
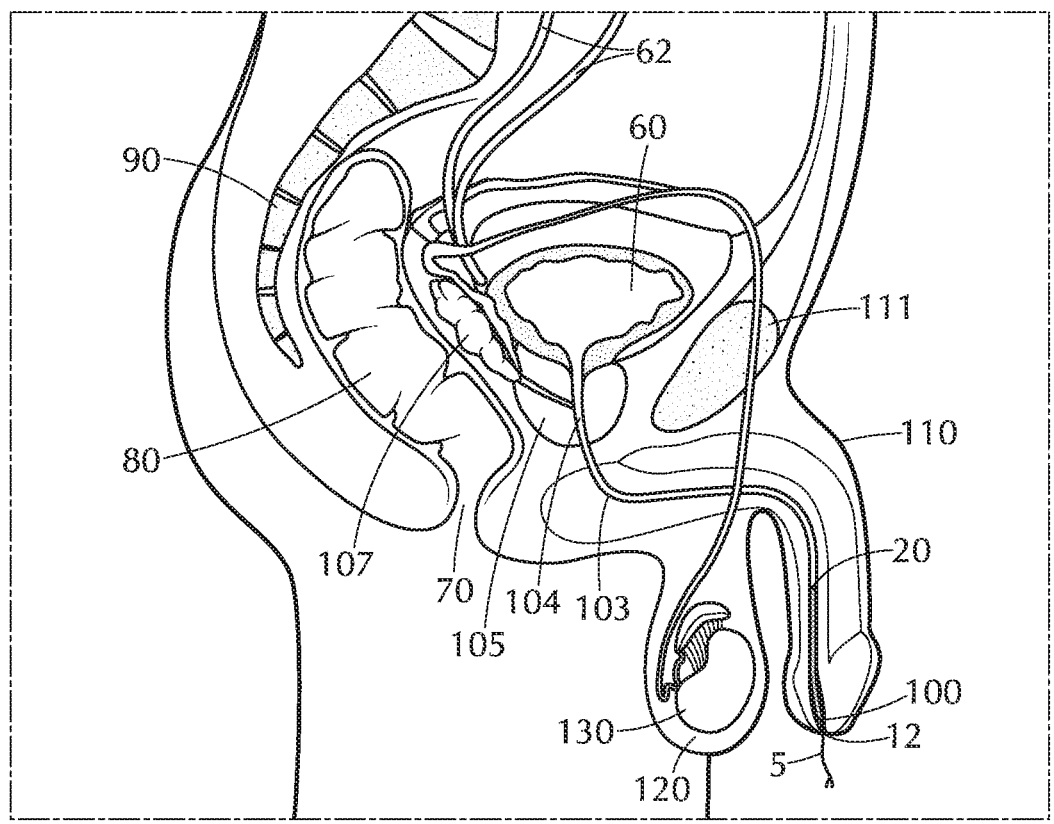
FIG. 3 is cross section of a male pelvis, showing an absorbent device inserted into urethra.

FIG. 3 shows a cross-section of a male pelvis in which an inventive device 100 is inserted. The external male pelvic organs include the penis 110, scrotum 120 and testicle 130. The male urethra is a muscular tube that runs from the bladder 60, through the prostate 105 and penis 110. The pubic symphysis 111 is situated between the bladder 60 and abdominal wall. Like females, the males have ureters 62, a urethral meatus 10 and anterior urethra 20. Males additionally have a Bulbar urethra 104 and bulbo-membraneous urethra 104 between the anterior urethra 20 and the Prostate 105. Seminal vesicle 107 lies on the posterior surface of the urinary bladder 60. The anus 70, rectum 80 and coccyx 90 run along the posterior side. An inventive device suitable for males 100 is positioned in the anterior urethra.

Average diameter for male and female urethral openings is about 4 to 8 mm. The diameter of the absorbent device can be 4 mm, 5 mm, 6 mm, 7 mm and 8 mm. The most commonly sized device is about 5 mm. The French (Fr) scale is used to measure the diameter of urethral catheters, and in turn the diameter of the urethra. The diameter in mm (D) of the urethra is Fr/3 (D=Fr/3). The most common urethral catheters used are 14, 16, 18, 20, 22 Fr catheters, although catheters from 8 to 30 Fr are available. There are some uncommon conditions where urethral diameter may be less than 3 mm or more than 8 mm.

The cylindrical body 4 is preferably about 4-8 mm in diameter by about 3-5 cm in length. In alternative embodiments, there could be opportunity to scale device to the range of French catheter sizes. In contrast, a typical compressed tampon for vaginal use is 30-60 mm in length and 8-20 mm wide. Typical dimensions of a vaginal tampon pledget before compression may be about 40 mm to about 100 mm in length and about 40 mm to about 80 mm in width. Generally, the inventive device material may be about 40 mm to about 60 mm in length and about 50 mm to about 70 mm in width.

Other sizes and configurations are contemplated for other types of mammals, which will be dependent on the species. For instance, it is envisioned that the inventive devices could be adapted and useful for those with incontinent pet dogs and cats. Those skilled in the veterinary arts will have suitable knowledge to adapt the shape and size appropriately.

Because of the need for absorbent capacity, the body 4 of the absorbent devices may be formed from batts much larger in size than the urethral orifice, and compressed to the small size indicated above in order to facilitate insertion. The body containing absorbent material 13 may be compressed in the radial direction, the axial direction, or both, to provide a body 4 which is of a size and stability to allow insertion within a urethra. The body 4 may be compressed in both the radial and axial direction using any means known in the art. While a variety of techniques are known and acceptable for these purposes, a modified tampon compressor machine available from Hauni Machines, Richmond, VA, is suitable.

FIG. 4 shows a cross section of the device of FIG. 1, which is suited to the female urethra. The body 4 contains an outer layer 6, a mesh 3 positioned round the outer layer 6, an intermediate layer 7 and absorbent core material 13 within the intermediate layer.

The outer layer 6 is exemplarily comprised of desiccated cotton. The intermediate layer 7 is comprised of desiccated chitosan or other cellulose bio sponge material.

The absorbent core material 13 may be comprised of superabsorbent polymer (SAP) or nanofiber. In preferred embodiments, the absorbent core material contains hydrogel properties. Although depicted as a plurality of rectangular discrete units, the absorbent core material 13 may take many forms. The absorbent core material may be contained in beads, capsules or sachets that are dispersed throughout the body 4 in a variety of configurations. The beads, capsules or sachets can take any shape. The absorbent core material may also be a SAP crystal, powder, fiber, or gel that is distributed in a homogenous or heterogenous manner.

In FIG. 4, the absorbent core 13 is comprised of a single layer of absorbent material 13 spread consistently along the radial axis. In contrast, FIG. 6 shows a configuration of absorbent the absorbent core that is suited to the male urethra. Due to the longer length of the male uretha, and consequently a suitable absorbent device e.g. 100, it is preferable to disperse the absorbent core along the longitudinal axis.

FIGS. 7A-7D show the interior of an exemplary device 300 having outer layer 304 of the substantially cylindrical body that has depressions of various topography. The body also contains intermediate layers 301, 302; absorbent core 303; and string 305. The outermost surface of the outward layer 304 can contain a mesh as in the aforementioned embodiments. The absorbent core 303 is comprised of two different types of material with one encasing the other. The materials may be the same as those described for FIGS. 1 and 4.

Preferably, the outer layer 301 is comprised of desiccated cotton and the intermediate layer 302 is comprised of desiccated chitosan or other cellulose/bio-sponge material. The absorbent core 303 is super absorbent polymer (SAP). The string 305 is comprised of cotton. The encasing mesh 304 is a polyethylene mesh.

Other examples of suitable depressions can be seen in tampons having a non-uniform topography, such as in U.S. Pat. No. 3,695,270 (Dostal, issued Oct. 3, 1972), and U.S. Pat. No. 4,361,151 (Fitzgerald, issued Nov. 20, 1982) and U.S. Pat. No. 4,328,804 (Shimatani, issued May 11, 1982), U.S. Pat. No. 5,403,300 (Howarth, issued Apr. 4, 1995), U.S. Pat. No. 5,592,725 (Brinker, issued Jan. 14, 1997)), U.S. Pat. No. 5,718,675 (Leijd, issued Feb. 17, 1998). Other tampons include longitudinal ribs on the outer surface, and in U.S. Pat. No. 7,549,982, the tampon has a spiral groove on the outer surface. All such surface topography is contemplated for the urethral devices described herein.

Texturing can be provided through a variety of means, including a multiplicity of texturing elements. Such texturing may be provided by needle punching the surface of the surface to be textured.

Texturing elements may also be configured to transfer fluid from the urethral surfaces to the outer surface of the body and ultimately, to the absorbent core through the use of a density gradient, hydrophilicity gradients, an osmotic driving force, capillarity, or a similar mechanism. Suitable materials for use in such fluid acquisition/transfer mechanisms are rayon (including, e.g., WO 00/06070 conventional, tri-lobed or multi-lobed rayon fibers), polyethylene, polypropylene, polyester, synthetic bi-component fibers, absorbent foams and combinations thereof, all of which fibers may be used either singly or in combination with other fibers are known in the art. Capillary channel fibers are a highly preferred fiber for texturing elements.

Figure 8:
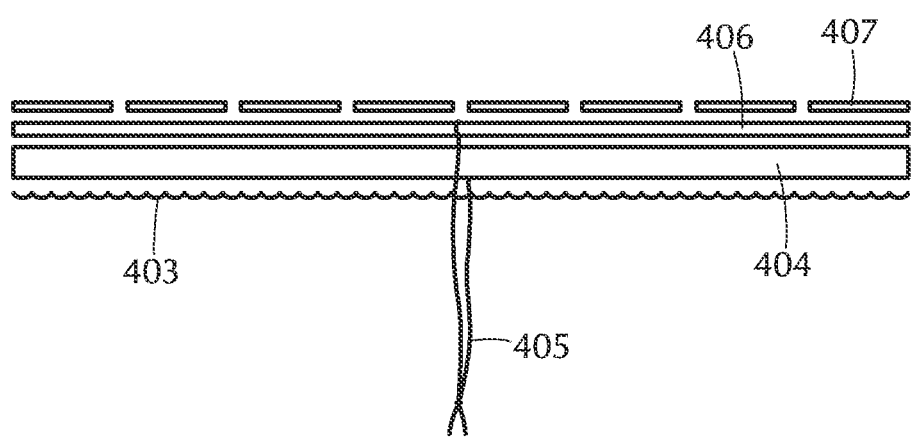
FIG. 8 is an unraveled distal end view of a device of the invention.

FIG. 8 shows an unraveled side view of another device wherein: 407 is super absorbent polymer (SAP) or nanofiber; 406 is desiccated chitosan or other cellulose/bio-sponge material; 404 is desiccated cotton; 405 is cotton string and 403 is polyethylene mesh covering.

In order to absorb urine in an incontinent individual, the inventive devices may be inserted digitally or through the use of known applicators.

Any of the currently available types of tampon applicators may be used for insertion of the absorbent devices of the present invention, with appropriate modification to accommodate the decreased size of the absorbent devices. Such applicators are typically a "tube and plunger" type arrangement and may be plastic, paper, or other suitable material. Additionally, a "compact" type applicator is also suitable. The applicator plunger will push the absorbent device out of the applicator due to the compressed nature of the core.

Figure 9A:
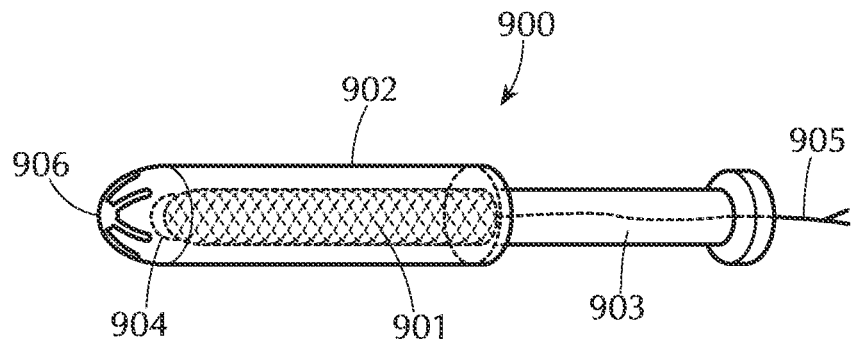
FIG. 9A is a perspective view of an applicator that can be utilized in the inventive devices.

FIG. 9A is an embodiment of an applicator 900 that may be utilized with the inventive devices wherein 901 is a cylindrical absorbent device having mesh that is housed in the interior of the applicator head 902. Abutted to the withdrawal side of the applicator is a removable plunger 903. A receptacle 904 is disposed at the insertion side of the applicator head 902 and is in fluid communication with an aperture at the tip of the insertion side. The receptacle may be filled with one or more of a lubricant, anesthetic jelly or an active agent.

Figure 9B:
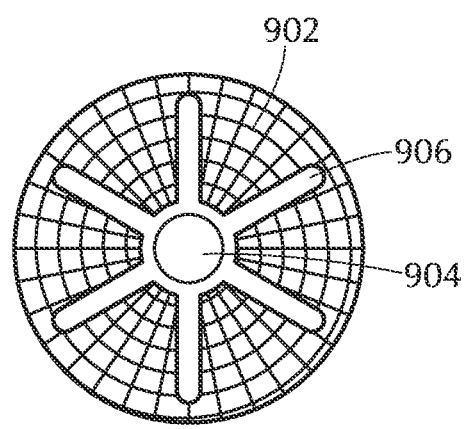
FIG. 9B is a proximal end view of the applicator of FIG. 9A.

FIG. 9B shows the receptacle 904 filled with hydrophilic anesthetic jelly. The jelly and device 901 are pushed through an optional notched flange 906 at the aperture of the receptacle and the insertion end of the applicator head 902.

It is anticipated the aforementioned devices are suitable to address incontinence issues in male and female mammals and ED in males. The devices should be changed at regular intervals to avoid infection.

Figure 10A:
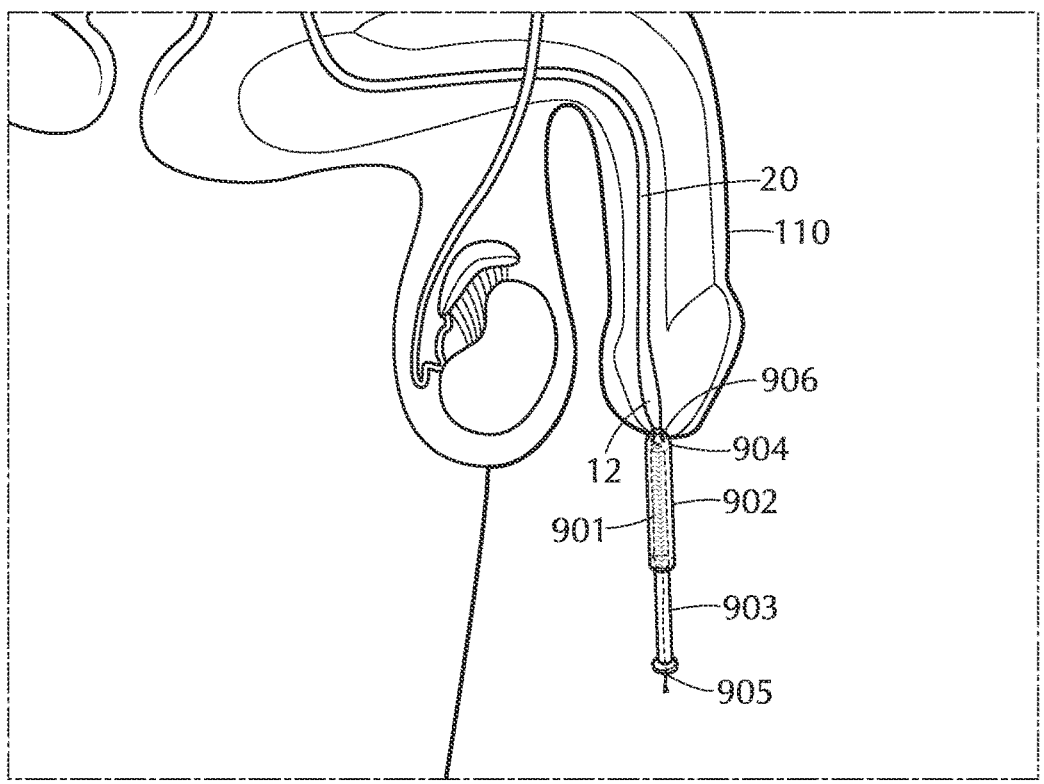
FIGS. 10A-10E show a method of treating incontinence in a male using an inventive device.
Figure 10B:
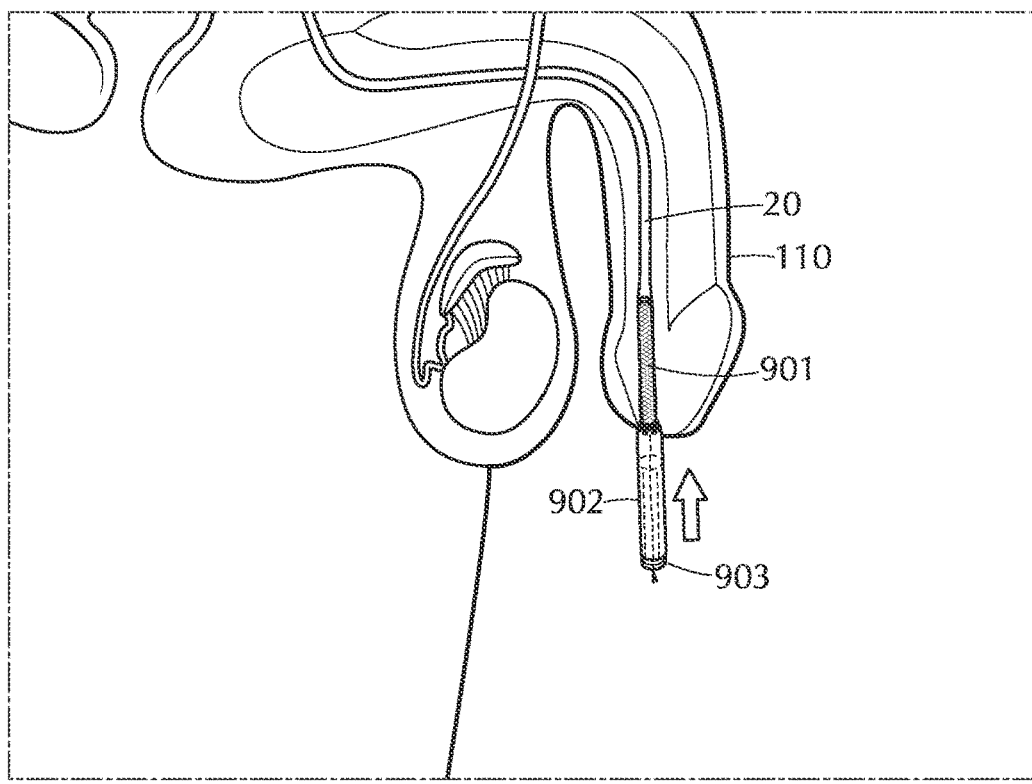

FIGS. 10A-10E show an exemplary method of treating urinary incontinence and ED in a human male patient using a device as shown in FIG. 9A. Referring to FIG. 10A, an applicator, such as 900 containing device 901, is used to place device 901 into a male urethra. The receptacle 904 contains lubricant and, if treatment of ED is desired, a vasodilator such as alprostadil. Alternatively, alprostadil can be impregnated in the device. The tapered applicator tip 906 is placed at the urethral opening with the plunger 903 fully extended out the distal end. As shown in FIG. 10B, the plunger 903 is compressed in the proximal direction, pushing the absorbent device 901, lubricant and alprostadil into the urethral meatus 12. The force used to push the plunger will squeeze the lubricant containing alprostadil in receptable 904 against the applicator head, popping it and coating the insertion tip of the device 901 as it moves into the meatus 12. Alternatively, a patient could pop receptacle 904 between fingers before placing device.

It is also envisioned that the patient could add additional lubricant, as desired, to the insertion tip of the device prior to placing at the urethral opening or squeeze an ampule containing active agent onto the applicator head. It is further envisioned that lubricant could be contained in a first receptacle having a low burst strength and active agent could be contained in a second receptacle that would dissolve or become permeable upon exposure to bodily fluid, such that the agent would only release upon insertion into the urethra or after being in contact with the lubricant for several minutes. This embodiment would be useful for agents that have a tendency to degrade upon exposure to lubricant.

Figure 10C:
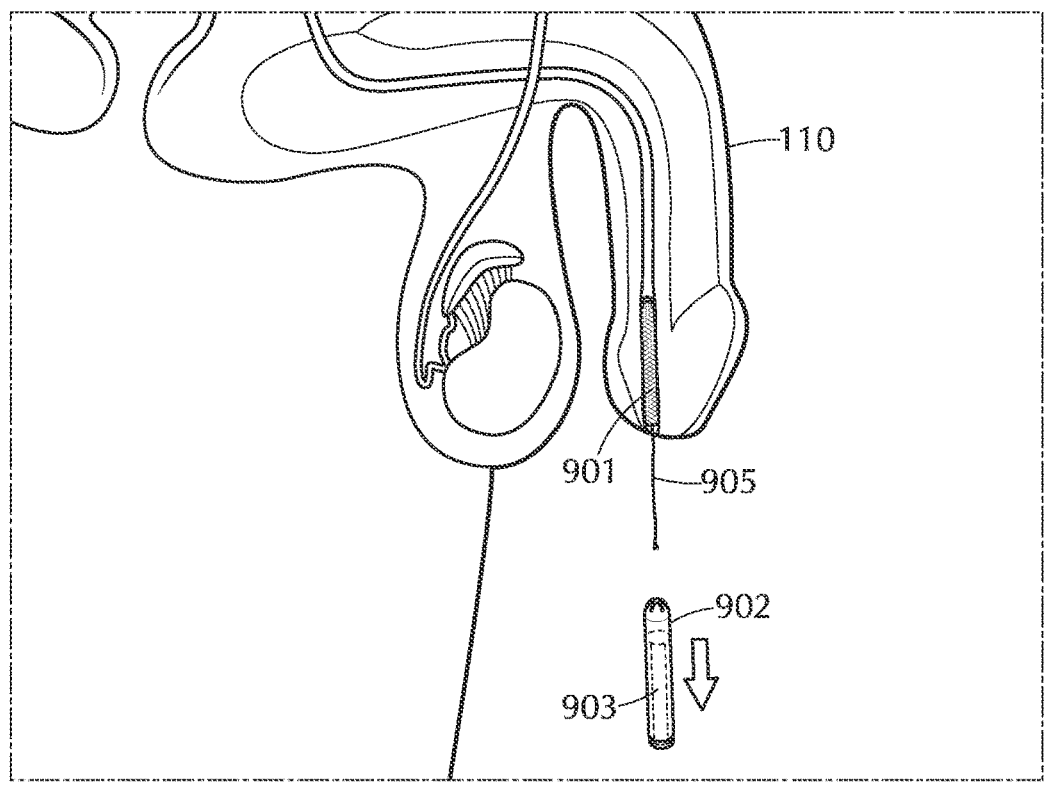
Figure 10D:
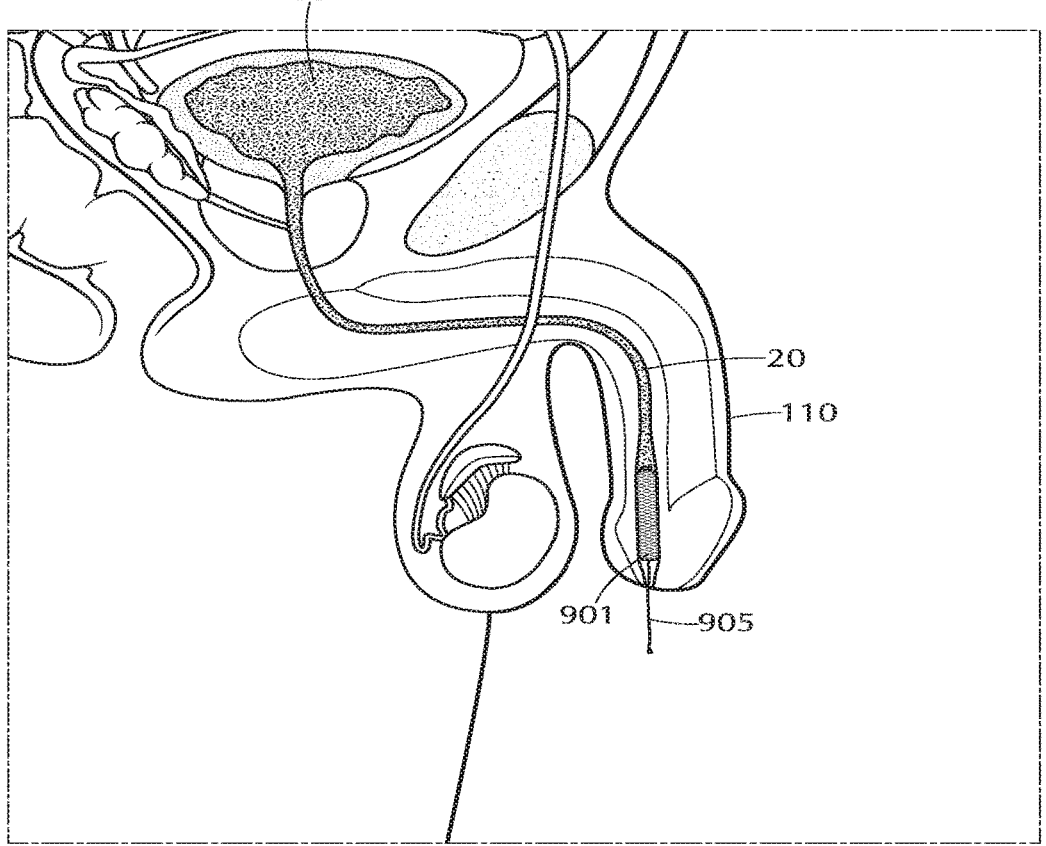
Figure 10E:
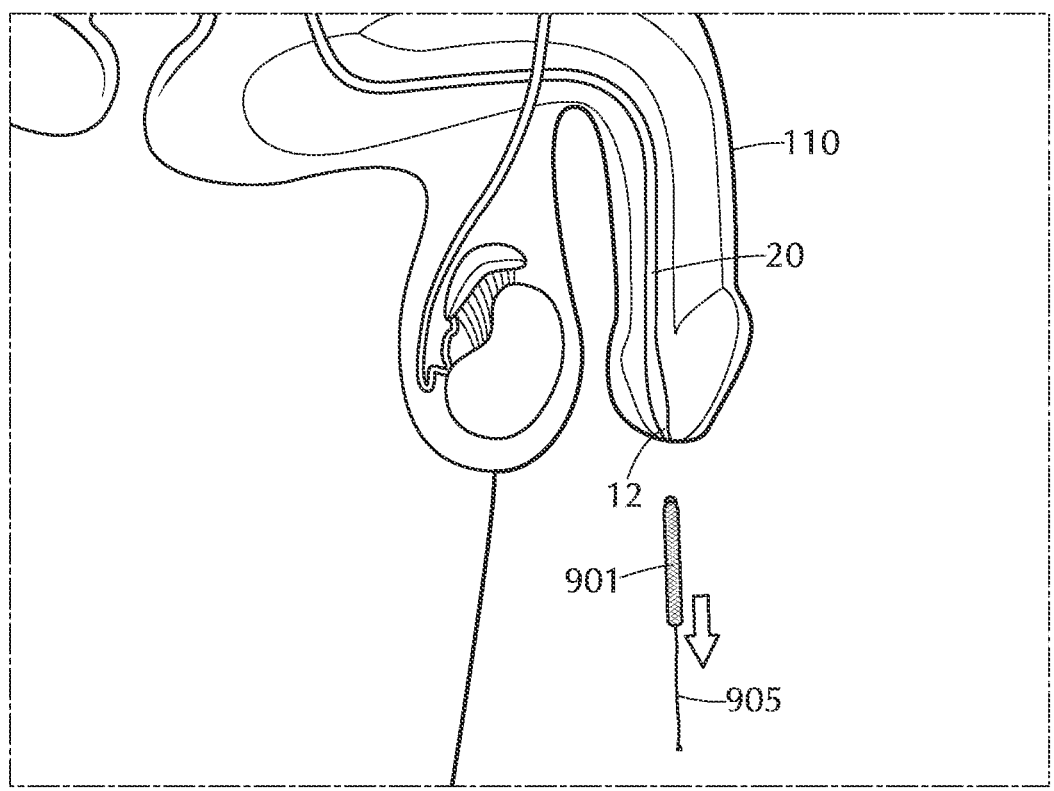

Next, as depicted in FIG. 10C, the lubricated device will remain in the meatus and the applicator body 902 containing the plunger 903 within it can be pulled distally and out of the urethral opening. As shown in FIG. 10D, the device 901 will absorb urine and bodily fluid and expand as it absorbs the fluids. As shown in FIG. 10E, when the device feels expanded and full (or after about 6 hours if there is no urination), the string 905 can be used to remove the device 901 from the urethra. The process can be repeated with a fresh, unimpregnated device as the patient desires to control incontinence.

Alternatively, if treating ED, the device containing a vasodilator, i.e. alprostadil, should be inserted about 30-60 minutes prior to sexual activity. The device should remain in the urethra for 5-20 minutes and then be removed by pulling on string 905. Alternatively, a patient may have sexual activity with device remaining in the urethra. A device comprising alprostadil should not be use more than three times a week and the patient should wait at least 24 hours between each use.

Figure 11A:
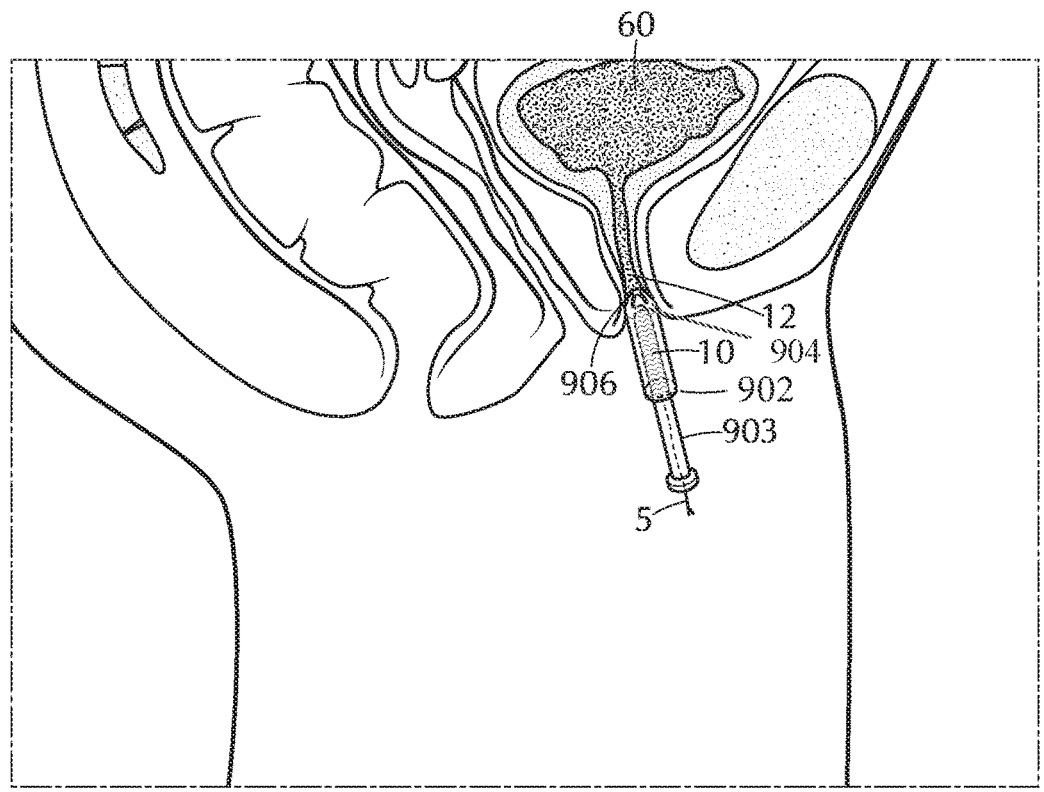
FIGS. 11A-11D show a method of treating incontinence in a female using an inventive device.
Figure 11B:
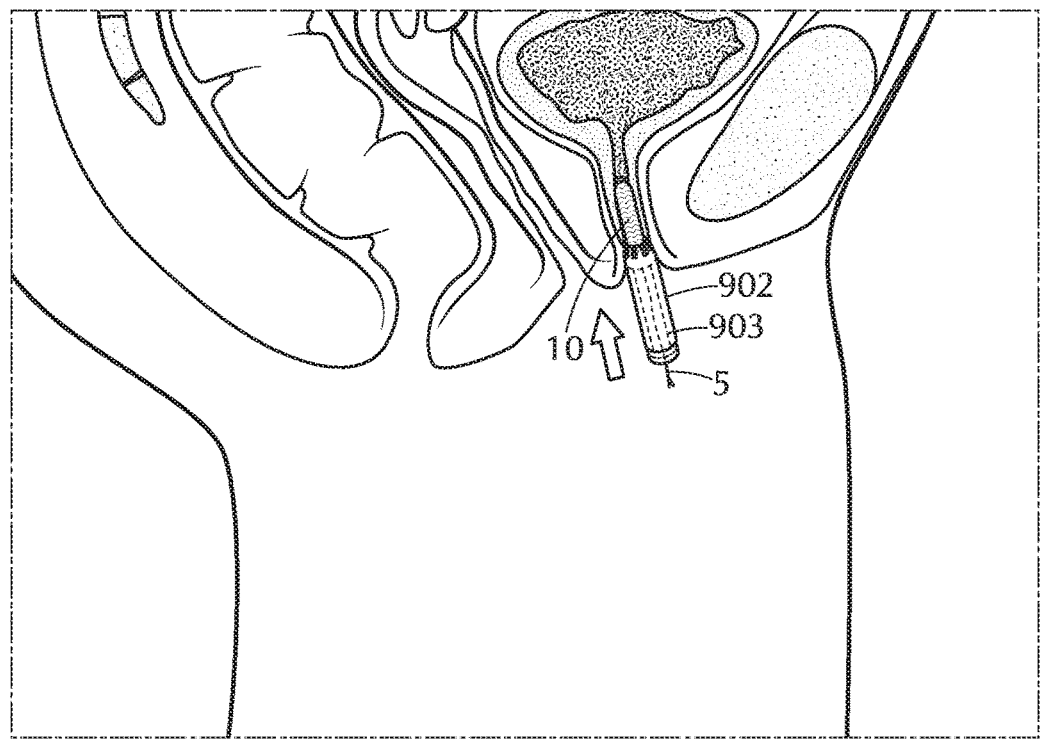

FIGS. 11A-11D show a method of treating incontinence in a female using device 10. A plunger similar in design to 900 is used but with the head 902 adapted to accommodate the shorter length of device 10. The tip 906 is placed at the urethral opening with the plunger 903 fully extended out the distal end. As shown in FIGS. 11A and 11B, the plunger 903 is compressed in the proximal direction, pushing the absorbent device 10 into the urethral meatus 12. The force used to push the plunger will squeeze the lubricant in receptable 904 against the head 906 popping it and coating the insertion tip of the device 10 as it moves into the meatus 12. Alternatively, a patient could pop receptacle between fingers just before placing device.

As with the male, it is also envisioned that the patient could add additional lubricant, as desired, to the insertion tip of the device prior to placing at the urethral opening.

Figure 11C:
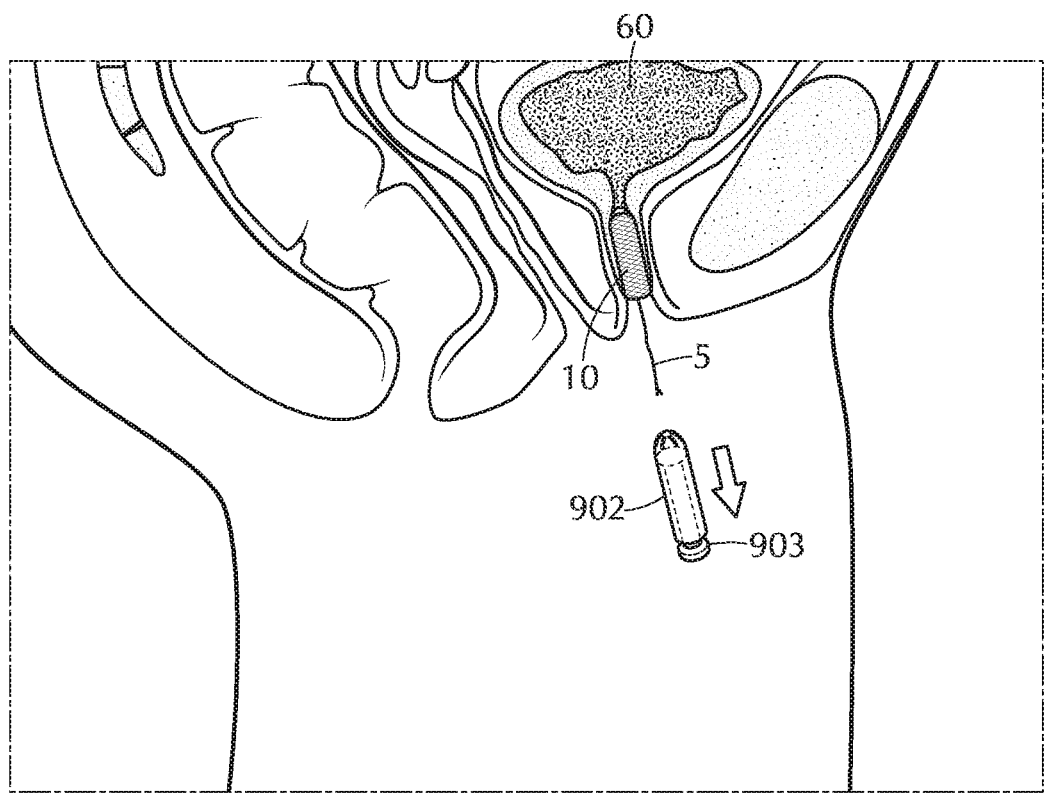
Figure 11D:
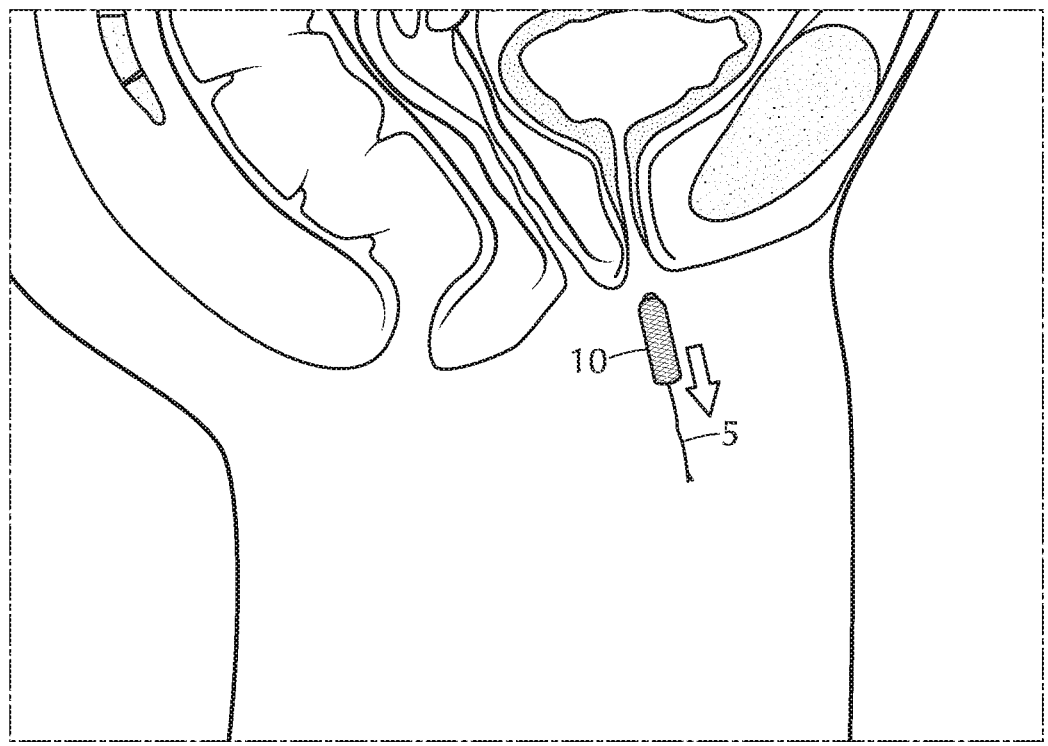

Next, as depicted in FIG. 11C, the lubricated device will remain in the meatus and the applicator body 902 containing the plunger 903 within it can be pulled distally and out of the urethral opening. The device 10 will absorb urine and expand as it absorbs urine, as shown in FIG. 11C. As shown in FIG. 11D, when the device feels expanded and full (or after about 6 hours if there is no urination), the string 5 can be used to remove the device 10 from the urethra. The process can be repeated with a fresh, unimpregnated device as the patient desires to control incontinence.

Although methods of addressing incontinence have been shown utilizing an applicator to insert the absorbent devices, it is also contemplated that a patient may easily be able to place desiccated device into urethra alone, without using applicator.

Further, although the foregoing explanations have focused on embodiments of absorbent devices for light incontinence, it should be understood that the present invention may be applied to uses ranging from extremely light incontinence to more severe, by simply changing the materials explained in the embodiments herein.

Another opportunity to use the inventive device is in the ureter. Patients who present with low grade urothelial cancer, or carcinoma in situ of the upper urinary tract often progress to nephroureterectomy because, unlike in the bladder, there is no effective way to allow chemotherapeutic agents to dwell in the ureter.

EXAMPLES

Patient W is a healthy sixty year old female with total urinary incontinence. She is s/p radical robotic cystectomy with creation of orthotopic ileal neobladder 6/2018 and has been incontinent since that time. She wears several pads/day. Although she would like to be sexually active she cannot due to leakage issues. W/u of incontinence revealed no evidence of fistula. She has tried bulking agent in urethra, as well as two f/u operations using rectus fascia to close and support urethra which have failed. She has failed intra-vaginal devices placed to occlude her urethra (Poise Impressa). She refuses to wear an indwelling foley catheter. She refuses abdominal surgery to close urethra and create either continent cutaneous stoma she can catheterize, or creation of non-continent urinary diversion.

Patient X is a healthy 51 year old male s/p radiation therapy to prostate for prostate cancer, s/p radical robotic cysto-prostatectomy with creation of Indian Pouch urinary reservoir for secondary bladder cancer. He is able to catheterize Indian Pouch for several hundred cc but also wears an ostomy appliance for sporatic stomal leakage.

Patient Y is an 87 year old male with total urinary incontinence following radiation therapy to prostate several years ago. He wears a Cunningham clamp to control his incontinence.

Patient Z is a healthy, 40 year old female runner, with significant urinary leakage every time she exercises. She has developed "diaper rash" from incontinence related to pad use, but does not want surgical intervention.

Patient W, X, Y and Z are suitable for treatment with the inventive devices. With sensation of bladder or pouch fullness, or based on a preset timed schedule, e.g. every 6 hours, (if no bladder fullness sensation is noted) the inventive urethral devices could be easily removed, and new GU device replaced.

Patient A is a 43 year old male with progressive ED due to hypertension and diabetes. Viagra and other PDE5 inhibitors work only for a short while. He does not want to use a vacuum pump. He does not want to try penile injection therapy. He has tried MUSE but can't sustain erection. He does not want surgery to place an inflatable penile prosthesis.

Patient B is a 65 year old male who had normal erectile function until he underwent radical prostatectomy for prostate cancer. He also has tried the above mentioned ED treatments without success. He wishes there was a new option to treat his ED, short of proceeding with prosthetic surgery.

Patient C is a 72 year old male s/p radiation therapy for prostate cancer. He has failed available treatment options to improve erectile function. He wishes there was new therapy to manage his ED.

Patients A, B, and C are good candidates for treatment with inventive device. They are motivated men with good performance status who would like to try a new available therapy to treat their ED, short of proceeding with surgery.

Detailed embodiments of the present invention are disclosed herein; however, it is to be understood that the disclosed embodiments are merely exemplary of the invention that may be embodied in various forms. It will be appreciated that many modifications and other variations that will be appreciated by those skilled in the art are within the intended scope of this invention as claimed below without departing from the teachings, spirit and intended scope of the invention.

What is claimed is:

1. A kit for treating urinary incontinence comprising:
    a device having
        a substantially cylindrical body having an insertion end and a withdrawal end, said body comprised of absorbent hydrogel material to absorb urine in a urethra, and
        a string attached to and exiting the withdrawal end of the body for removing the device from the urethra; and
    an applicator adapted for inserting the device into the urethra of a human.

2. The kit of claim 1, wherein the device body comprises an outer layer, an intermediate layer and an inner layer, said intermediate and inner layers comprising the hydrogel material.

3. The kit of claim 1, further comprising a mesh encasing the body.

4. The kit of claim 3, wherein the mesh is comprised of polyethylene and/or polyurethane.

5. The kit of claim 1, further comprising a biodegradable receptacle at the insertion end of the body, and a lubricating material within the receptacle.

6. The kit of claim 5, wherein the lubricating material is an anesthetic jelly.

7. The kit of claim 5, wherein the lubricating material comprises an antibiotic.

8. The kit of claim 1, wherein the device is impregnated with an antibiotic.

9. The kit of claim 1, wherein the device comprises a vasodilator comprised in or on the body of the device and/or the applicator.

10. The kit of claim 1, wherein the absorbent hydrogel material comprises super absorbent polymer (SAP).

11. The kit of claim 1, wherein the device diameter is about 4-8 mm.

12. The kit of claim 1, wherein the device length is about 3-5 cm.

13. The kit of claim 1, wherein the applicator contains lubricant.

14. A kit for treating erectile dysfunction comprising:
    a device having
        a substantially cylindrical body having an insertion end and a withdrawal end, said body comprised of absorbent material, and
        a string attached to and exiting the withdrawal end of the body for removing the device from the urethra;
    an applicator adapted for inserting the device into the urethra of a male human; and
    a vasodilator comprised in or on the body of the device and/or the applicator.

15. The kit of claim 14, wherein the vasodilator is alprostadil.

16. A kit for treating urinary incontinence comprising:
    a device having
        a substantially cylindrical body having an insertion end and a withdrawal end, said body comprised of absorbent material to absorb urine in a urethra, and
        a string attached to and exiting the withdrawal end of the body for removing the device from the urethra; and
    an applicator adapted for inserting the device into the urethra of a human,
    wherein the device diameter is about 4-8 mm.

* * * * *